(12) United States Patent
Bullinga et al.

(10) Patent No.: US 9,968,783 B2
(45) Date of Patent: May 15, 2018

(54) TREATMENT FOR CARDIAC CONDUCTANCE ABNORMALITIES

(71) Applicants: DREXEL UNIVERSITY, Philadelphia, PA (US); John R. Bullinga, Philadelphia, PA (US)

(72) Inventors: John R. Bullinga, Philadelphia, PA (US); Allon Guez, Narbeth, PA (US)

(*) Notice: Subject to any disclaimer, the term of this patent is extended or adjusted under 35 U.S.C. 154(b) by 0 days. days.

(21) Appl. No.: 14/781,433

(22) PCT Filed: Apr. 4, 2014

(86) PCT No.: PCT/US2014/032597
§ 371 (c)(1),
(2) Date: Sep. 30, 2015

(87) PCT Pub. No.: WO2014/165745
PCT Pub. Date: Oct. 9, 2014

(65) Prior Publication Data
US 2016/0051822 A1  Feb. 25, 2016

Related U.S. Application Data

(60) Provisional application No. 61/808,389, filed on Apr. 4, 2013.

(51) Int. Cl.
*A61N 1/37* (2006.01)
*A61N 1/36* (2006.01)
*A61F 2/82* (2013.01)

(52) U.S. Cl.
CPC ............ *A61N 1/36114* (2013.01); *A61F 2/82* (2013.01); *A61F 2002/821* (2013.01)

(58) Field of Classification Search
CPC ........ A61N 1/05; A61N 1/056; A61N 1/0565; A61N 1/0568; A61N 1/36017
See application file for complete search history.

(56) References Cited

U.S. PATENT DOCUMENTS

| | | | |
|---|---|---|---|
| 5,111,811 A * | 5/1992 | Smits | A61N 1/056 607/125 |
| 5,609,615 A | 3/1997 | Sanders et al. | |
| 5,873,896 A | 2/1999 | Ideker | |
| 6,999,821 B2 | 2/2006 | Jenney et al. | |
| 7,317,950 B2 | 1/2008 | Lee | |

(Continued)

OTHER PUBLICATIONS

Bidez, et al., "Polyaniline, an Electroactive Polymer, Supports Adhesion and Proliferation of Cardiac Myoblasts", J Biomater Sci Polym Ed., 2006, 17(1-2), 199-212.

(Continued)

*Primary Examiner* — Michael Carey
*Assistant Examiner* — Natasha Patel
(74) *Attorney, Agent, or Firm* — Joseph E. Maenner; Maenner & Associates, LLC

(57) ABSTRACT

Methods and apparatuses are provided for treating cardiac conductive disorders that include implantation of a network of material that adaptively corrects the electrical conductivity of heart tissues and restores "normal" conductance. The methods and apparatuses disclosed herein involve the delivery of a material to a subject's heart in order to restore normal conductance in a minimally invasive, tunable, localized, and reversible manner, without artificial electrical stimulation.

16 Claims, 1 Drawing Sheet

(56) References Cited

U.S. PATENT DOCUMENTS

| | | | |
|---|---|---|---|
| 7,502,652 | B2 | 3/2009 | Gaunt et al. |
| 7,881,808 | B2 | 2/2011 | Borgaonkar et al. |
| 2002/0188170 | A1* | 12/2002 | Santamore ....... A61B 17/00234 600/37 |
| 2004/0010180 | A1* | 1/2004 | Scorvo ................ A61F 2/2481 600/16 |
| 2007/0083075 | A1* | 4/2007 | Ein-Gal ................ A61B 18/14 600/13 |
| 2007/0129761 | A1 | 6/2007 | Demarais et al. |
| 2009/0105796 | A1 | 4/2009 | Atanasoska et al. |
| 2013/0190848 | A1* | 7/2013 | Moss ...................... A61N 1/05 607/116 |
| 2013/0204311 | A1* | 8/2013 | Kunis ..................... A61F 2/885 607/14 |

OTHER PUBLICATIONS

Estner, et al., Electrical Isolation of Pulmonary Veins in Patients with Atrial Fibrillation: Reduction of Fluoroscopy Exposure and Procedure Duration by the use of a Nonfluoroscopic Navigation System, Europace, Jul. 2006, 8, 583-587.

Fuster, et al., "ACC/AHA/ESC 2006 Guidelines for the Management of Patients with Atrial Fibrillation: A Report of the American College of Cariology/American Heart Association Task Force on Practice Guidelines and the European Society of Cardiology Committee for Practice Guidelines", J. Am Coll Cardial., Aug. 2006, 48(4), 854-906.

Guimard, et al., "Conducting Polymers in Biomedical Engineering", Prog. Polym. Sci., 32(8-9), Sep. 2007, 876-921.

Haissaguerre, et al., "Spontaneous Initiation of Atrial Fibrillation by Ectopic Beats Originating in the Pulmonary Veins", N Engl. J. Med., Sep. 1998, 339(10), 659-666.

Igarashi, et al., "Coonexin Gene Transfer Preserves Conduction Velocity and Prevents Atrial Fibrillation", Circulation, Jan. 2012,125(2), 216-225.

Jais, et al., "A Focal Source of Atrial Fibrillation Treated by Discrete Radiofrequency Ablation", Circulation 1997, 95, 572-576.

Krummen, et al., "Centrifugal Gradients of Rate and Organization in Human Atrial Fibrillation", Pacing Clin. Electrophysiol., Sep. 2009, 32(11), 1366-1378.

Li, et al., "Electrospinning Polyaniline-Contained Gekatin Nanofibers for Tissues Engineering Applications", Biomaterials, May 2006, 27(13), 2705-15.

Moe, et al., "A Computer Model of Atrial Fibrillation", Am Heart J., 1964, 200-220.

Novak, et al., "Utility of a Nonfluoroscopic Navigation System for Pulmonary Vein Isolation", J Cardiovasc Electrophysiol, Aug. 2004, 15(8), 967.

Pappone, et al., "A Randomized Trial of Circumferential Pulmonary Vein Ablation Versus Antiarrhythmic Drug Therapy in Paroxysmal Atrial Fibrillation: The APAF Study", J. Am Coll Cardio, Dec. 2006, 48(11), 2340-2347.

Park, et al., "A Novel Composite Scaffold for Cardiac Tissue Engineering", Anim., Apr. 2005, 41(7), 188-196.

Ramanathan, et al., "Electrocardiographic Imaging (ECGI): A Noninvasive Imaging Modality for Cardiac Electrophysiology and Arrhythmia", Nature Medicine, 2004; 10, 422-428.

Waktare, et al., "Cardiology Patient Page, Atrial Fibrillation", Circulation, 2002; 106(1), 14-16.

You, et al., "Nanoengineering the Heart: Conductive Scaffolds Enhance Connexin 43 Expression", Nano Lett., Aug. 2011, 11(9), 3643-3648.

* cited by examiner

TREATMENT FOR CARDIAC CONDUCTANCE ABNORMALITIES

CROSS-REFERENCE TO RELATED APPLICATIONS

This application is a National Stage Application pursuant to 35 U.S.C. § 371 of International Application No. PCT/US2014/032957, filed Apr. 4, 2014, which claims the benefit of priority to U.S. Provisional Patent Application Ser. No. 61/808,389, filed Apr. 4, 2013, which is herein incorporated by reference in its entirety.

TECHNICAL FIELD

The present disclosure relates to the use of a conductance-modulating array in apparatuses and methods for correcting cardiac conductance abnormalities.

BACKGROUND

The essential function of the heart is to pump blood to the body. The major cellular constituents of the heart are cardiac fibroblasts, cardiomyocytes, endothelial cells, and vascular smooth muscle cells. During cardiogenesis, some cardiomyocytes are further differentiated into the specialized conduction system consisting of the sinus node, AV node, and HIS-Purkinje system. Cardiomyocytes and the specialized conduction system are the electrically active cells of the heart. The heart is both an electrical and a mechanical organ in which cellular membrane potentials control initiation of mechanical contraction followed by relaxation. The coordinated electrical activity results in mechanical contraction and the pump function of the heart. Under normal conditions, heartbeats are initiated by depolarizing pacemaker currents in the sinus node that then depolarize sequential neighboring cardiomyocytes in the atrium resulting in a depolarization wavefront across the atrium. The wavefront of depolarization then depolarizes as the AV node which sequentially depolarizes the His-Purkinje system and then the ventricular cardiomyocytes. Electrical depolarization initiates cardiac contraction of cardiomyocytes. Cellular ionic currents then result in electrical repolarization of each cell type and relaxation of cardiomyocytes. Repolarized cells are then available to become activated again with a depolarization wavefront for the next heart beat that is initiated by the sinus node.

The depolarization wavefront is dependent on cellular ionic currents with the inward sodium current being the dominant depolarization current and cell-to-cell connections know as gap junctions that allow transmission of electrical currents between cells. The principal gap junction proteins are connexins 40 and 43.

Disease states can result in slowing of the conduction velocity of the depolarization wavefront. Reentry is the most common mechanism of cardiac arrhythmias. The wavelength theory of arrhythmias suggests that reentry is more likely to occur when conduction velocity slows or refractoriness of cell is decreased. Additionally, disease states may result in cardiac fibrosis and dilatation of the atrium and ventricles. Areas of fibrosis may slow or block the depolarization wavefront. Dilatation of cardiac chambers prolongs the time required to depolarize each chamber and makes reentry more likely.

Treatment options for cardiac arrhythmias consists of antiarrhythmic drugs, ablation, and device therapy such as pacemakers and defibrillators. Most efforts in treating cardiac arrhythmias are to prolong repolarization and refractoriness to make reentry less likely. These include antiarrhythmic drugs such as amiodarone, sotalol, and dofetilide. Other efforts to treat cardiac arrhythmias consist of using ablation to block part of a circuit of reentry. Ablation and consists of destruction of cardiomyocytes with heating or cooling of tissue. Cardiomyocytes are then replaced with fibroblasts which are not electrically conductive once the tissue has healed. Correction of conduction delays by improving conduction velocity with Connexin gene transfer is another potential approach to treat arrhythmias (Igarashi, et al., *Circulation*. 2012; 125: 216-225), but this approach remains in early stages of research.

Disease states result in slowing of conduction velocity and dilation of cardiac chambers results in larger distances for wavefronts of depolarization to travel. The summation of slower conduction velocity and larger distances result in substantial conduction delays when compared to normal physiology. Additionally, disease states are often associated with blocks in the specialized conducting system such as the left bundle of the Purkinje system. Loss of the normal synchronization of electrical activation results and what is known as dyssynchrony. Dyssynchrony of electrical activation results in dyssynchrony of the mechanical activation and less efficient contraction of the heart. Correction of conduction delays that improve synchrony of electrical activation and subsequently mechanical activation may improve cardiac function. This is the principal behind resynchronization therapy that is currently performed using pacemakers with multiple pacing electrodes.

Conduction abnormalities can deprive the heart of normal functioning. They can, for example, disrupt normal synchrony and produce any of a number of different conduction disorders. Cardiac arrhythmias are a leading cause of morbidity in the Western hemisphere. The risk of developing malignant ventricular tachyarrhythmias is associated with the extent of myocardial injury and is believed to be the primary cause of approximately 50% of all cardiovascular deaths. Bradycardia and heart block, which can result from the normal aging process, further contribute to the morbidity associated with cardiac arrhythmias and result in permanent implantation of over 160,000 pacemakers annually in the United States. Atrial fibrillation is the most common cardiac arrhythmia and is characterized by rapid, irregular, uncoordinated depolarizations of the atria with no definite P waves. It can occur as a result of numerous different pathophysiological processes in the two upper chambers (atria) of the heart.

Several techniques or hypotheses have been deployed in the field for stabilizing cardiac arrhythmia. Most, however, are impractical or require a critical surgical procedure. In some instances, especially where the condition arises from a conduction disturbance that is due to ischemia, only radical options, such as surgery, are available. However, even surgical techniques can fall well short of the therapeutic goal of restoring cardiac function to the patient. For example, although a surgical procedure known as "maze" was designed to eliminate atrial fibrillation permanently, it gave rise to a number of complications. In the maze procedure, incisions are made with a scalpel in the walls of the atria in order to block electrical impulse conduction in a direction crosswise to the incisions, i.e., by interruption of the local tissue continuity. As a result of subsequent scarring, these electrical blocks acquire a permanent, irreversible character. However, the long duration of the operation creates a considerable risk of damage to the heart muscle.

Tissue engineering techniques generally involve transplanting cells that can imitate certain cardiac functions in to cardiac tissue in order to effect myocardial repair. One proposed technique attempts to establish electrical coupling between cardiomyocytes and recombinant cells that have been genetically engineered to express a connexin protein, such as connexin 43. See You, et al., *Nano Lett.* 2011, 11, 3643-3648.

Various antiarrhythmic drugs also have the potential to restore normal heart rhythm. These include quinidine, procainamide, disopyramide, flecainide, propafenone, dofetilide, ibutilide, azimilde, amiodarone, and sotalol. However, such medications are effective in only 30-60% of patients and in any event generally lose effectiveness over time. In addition, some antiarrhythmic drugs have the potential to produce serious side effects.

Anti-arrhythmic drugs and radiofrequency catheter ablation are presently the most commonly-used techniques for controlling atrial fibrillation. Radiofrequency ablation uses irreversible destruction of atrial tissue to attempt to block circuits of atrial fibrillation. The procedure is highly invasive and has significant procedural risk, and the results have substantial variability in clinical practice.

Correction of conduction abnormalities may be antiarrhythmic by improving synchrony of depolarization and making reentry more difficult to occur. Correction of conduction abnormalities may be therapeutic for restoration of synchrony and improve cardiac function. The approach of improving conduction may have advantages over antiarrhythmic drug therapy and ablation therapy. New methodologies that are at least partially curative, less invasive that existing techniques, reversible, and preferably tunable could represent viable treatment alternatives for thousands of affected individuals.

SUMMARY

The present disclosure pertains to methods for treating a cardiac conductance disorder in a subject comprising delivering an array comprising a conductance modulating material to at least one location of the subject's heart that corresponds to a conductance abnormality or an arrhythmogenic region in order to modulate conductance to a therapeutically useful degree to the at least one location without chronic artificial electrical stimulation.

Such methods may further comprise using a conductance map of the subject's heart to identify at least one location of the heart that corresponds to a conductance abnormality, using a map of electrical characteristics of the subject's heart in order to identify at least one location of a heart that corresponds to an arrhythmogenic region, or both. The methods may also or alternatively comprise determining one or more characteristics of a conductance abnormality or an arrhythmogenic region at an identified location of the subject's heart. In such embodiments, the methods may further comprise selecting a conductance modulating material for delivery to the identified location based on at least one determined characteristic of the conductance abnormality or an arrhythmogenic region at the identified location.

The methods according to the present disclosure may also comprise delivering the array to the endocardium or to the epicardium of the subject's heart. The array may be delivered to the endocardium of the subject's heart through a catheter. For example, the array may be delivered to the endocardium of the subject's left atrium. The array may also be delivered to the epicardium of the subject's heart, for example, through a surgical or percutaneous approach. For example, the array may be delivered to the epicardium of the subject's atrium to correct an atrial conduction problem. An array may also or alternatively be delivered to the epicardium of the subject's ventricle, for example, to correct a ventricular conduction problem.

The arrays according to the present methods may include a conductance modulating material that enhances electrical conductivity at a corresponding location of the subject's heart. Alternatively or additionally, the arrays may include a conductance modulating material that increases electrical resistance at a corresponding location of the subject's heart. The arrays according to the present methods may be expandable.

Also disclosed are methods that comprise implanting in a subject's heart an array comprising a conductance modulating material that is deployable to at least one location of the subject's heart that corresponds to a conductance abnormality or an arrhythmogenic region, and that is arranged in its deployed state to contact the location in order to modulate conductance to a therapeutically useful degree to the at least one location without chronic artificial electrical stimulation.

Such methods may further comprise using a conductance map of the subject's heart to identify at least one location of the heart that corresponds to a conductance abnormality, using a map of electrical characteristics of the subject's heart in order to identify at least one location of a heart that corresponds to an arrhythmogenic region, or both. The methods may also or alternatively comprise determining one or more characteristics of a conductance abnormality or an arrhythmogenic region at an identified location of the subject's heart. In such embodiments, the methods may further comprise selecting a conductance modulating material for delivery to the identified location based on at least one determined characteristic of the conductance abnormality or an arrhythmogenic region at the identified location.

The apparatuses according to the present disclosure may include a conductance modulating material that enhances electrical conductivity at a corresponding location of the subject's heart. Alternatively or additionally, the apparatuses may include a conductance modulating material that increases electrical resistance at a corresponding location of the subject's heart. The apparatuses according to the present methods may be expandable.

Another inventive embodiment pertains methods for treating a cardiac conductance disorder in a subject comprising a conductance modulating material that is deployable to at least one location of the subject's heart that corresponds to a conductance abnormality or an arrhythmogenic region, and is arranged in a deployed state to contact the location in order to modulate conductance to a therapeutically useful degree to the at least one location without chronic artificial electrical stimulation.

A further embodiment pertains to methods for modulating conductance in a subject's heart comprising delivering to the subject's heart an array that comprises a conductance modulating material and that has an unexpanded and an expanded state, wherein in the expanded state the array contacts at least one location of the subject's heart that corresponds to a conductance abnormality or an arrhythmogenic region and modulates conductance at the location to a therapeutically useful degree without chronic artificial electrical stimulation.

Yet another embodiment pertains to methods for modulating conductance in a subject's heart comprising delivering to said subject's heart an array that comprises a conductance modulating material and that has an unassembled and an assembled state, wherein in the assembled state the array contacts at least one location of the subject's heart that corresponds to a conductance abnormality or an arrhythmogenic region and modulates conductance at said location to a therapeutically useful degree without chronic artificial electrical stimulation.

The present apparatuses/arrays may be deployable to the subject's heart through a catheter. The apparatuses may be self-expanding. In some embodiments, the present apparatuses/arrays may comprise two or more discrete parts that may be assembled pursuant to deployment to the subject's heart. Assembly of such parts may result in a removable or permanent attachment between the parts. Some apparatuses may comprises three or more discrete parts, of which at least two undergo attachment during deployment to the subject's heart, and of which at least two remain unattached after deployment to the subject's heart. The apparatuses may comprise a conductance modulating material that enhances electrical conductivity at a location of said subject's heart that contacts said material. The apparatuses may alternatively or additionally comprise a conductance modulating material that increases electrical resistance at a location of said subject's heart that contacts said material. The conductance modulating material of the present apparatuses may comprise an electroactive polymer. The apparatuses may be arranged to at least partially correspond to a conductance map of said subject's heart.

DETAILED DESCRIPTION OF ILLUSTRATIVE EMBODIMENTS

Figure 1:
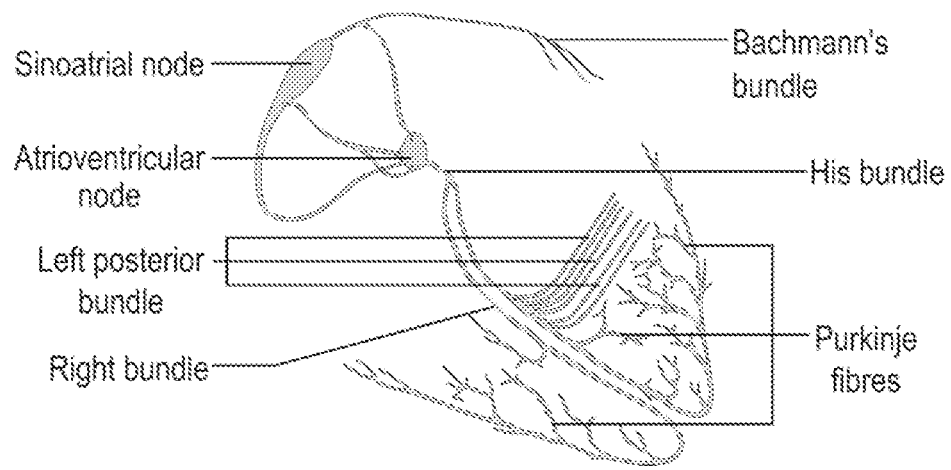
FIG. 1 depicts a generalized schematic of the specialized conductance system of a human heart.

The present inventions may be understood more readily by reference to the following detailed description taken in connection with the accompanying figures and examples, which form a part of this disclosure. It is to be understood that these inventions are not limited to the specific products, methods, conditions or parameters described and/or shown herein, and that the terminology used herein is for the purpose of describing particular embodiments by way of example only and is not intended to be limiting of the claimed inventions.

In the present disclosure the singular forms "a," "an," and "the" include the plural reference, and reference to a particular numerical value includes at least that particular value, unless the context clearly indicates otherwise. Thus, for example, a reference to "a material" may be a reference to one or more of such materials and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

Unless otherwise specified, any component, element, attribute, or step that is disclosed with respect to one embodiment of the present methods and products may apply to any other method or product that is disclosed herein.

The disclosures of each patent, patent application, and publication cited or described in this document are hereby incorporated herein by reference, in their entirety.

Numerous disorders of the heart arise from conductance abnormalities. The most common sustained arrhythmia is atrial fibrillation. Slowing of conduction due to aging and disease processes results in a state of increased risk of atrial fibrillation. Improvement of conduction may decrease the risk of atrial fibrillation. Conduction blocks such as left bundle branch block in the setting of patients with cardiomyopathy results and dyssynchrony and worsening of heart failure. Improvement of conduction may reduce dyssynchrony (provide resynchronization) and the risk of heart failure. However, due to the complicated mechanism of electrical propagation within the heart, existing methods may be ineffective for controlling or treating conductance abnormalities. The most common existing method, radiofrequency catheter ablation, is highly invasive, irreversible, and not curative.

The present disclosure pertains to new methods and apparatuses for treating cardiac conductive disorders that include implantation of a conductive and/or insulating network of material that adaptively corrects the electrical conductivity of heart tissues and restores "normal" conductance. Current methodologies permit the assessment of actual conductance patterns in a subject's heart, which in turn permits a determination of the ideal cardiac conductance pattern for that subject. Prior to the present disclosure, however, the means did not exist for restoring normal conductance within the heart. The methods and apparatuses disclosed herein involve the delivery of a material to a subject's heart in order to restore normal conductance in a minimally invasive, tunable, localized, and reversible manner, without artificial electrical stimulation.

In one embodiment, methods are disclosed for treating a cardiac conductance disorder in a subject comprising delivering an array comprising a conductance modulating material to at least one location of the subject's heart that corresponds to a conductance abnormality or an arrhythmogenic region in order to modulate conductance to a therapeutically useful degree to the at least one location without chronic artificial electrical stimulation. Also disclosed are methods that comprise implanting in or on a subject's heart an array comprising a conductance modulating material that is deployable to at least one location of the subject's heart that corresponds to a conductance abnormality or an arrhythmogenic region, and that is arranged in its deployed state to contact the location in order to modulate conductance to a therapeutically useful degree to the at least one location without chronic artificial electrical stimulation. A further embodiment pertains for modulating conductance in a subject's heart comprising delivering to the subject's heart an array that comprises a conductance modulating material and that has an unexpanded and an expanded state, wherein in the expanded state the array contacts at least one location of the subject's heart that corresponds to a conductance abnormality or an arrhythmogenic region and modulates conductance at the location to a therapeutically useful degree without chronic artificial electrical stimulation. The present disclosure also pertains to apparatuses for treating a cardiac conductance disorder in a subject comprising a conductance modulating material that is deployable to at least one location of the subject's heart that corresponds to a conductance abnormality or an arrhythmogenic region, and is arranged in a deployed state to contact the location in order to modulate conductance to a therapeutically useful degree to the at least one location without chronic artificial electrical stimulation.

It is known to provide medical devices that employ electrically conducting polymers, and many of these devices may be used for cardiac applications. For example, U.S. Pat. No. 5,609,615 discloses a cardiac stimulator partially fabricated from electrically conducting polymers. U.S. Pat. No. 6,999,821 discloses a body implantable lead including one or more conductive polymer electrodes for performing one or more of "pacing, sensing, cardioversion and defibrillation." U.S. Published Application No. 2009/105796 discloses a biomemetic electrode material including a fibrous matrix formed at least in part from conductive polymer for use "in a number of body-implantable application[s] including cardiac and neuron-stimulation applications." U.S. Pat. No. 7,881,808 discloses a cardiac electrode having a coating of which at least a portion comprises a conducting polymer. Additional publications disclose the implantation of conducting polymers for use as conductors of electrical signals within the heart or other body tissues. For example, U.S. Pat. No. 7,317,950 ("the '950 patent") discloses the injection of conducting agents, including polymers, into regions of cardiac tissue "in order to affect the conduction and enhance the response to electrical stimulation there" (see col. 13, lines 31-35). U.S. Pat. No. 7,502,652 ("the '652 patent") discloses the implantation of passive conductors in order to route electrical current along a desired path, wherein the material from which the conductor is made may be a conductive polymer.

However, no prior art publication discloses the use of conducting polymer for the transmission of electrical signals that the heart itself produces, for example, from the sinoatrial node. Both the '950 patent and the '652 patent specify that the electrical signal that the conductive polymer transmits does not originate from the subject's own body, but rather from artificial sources (see, e.g., '950 patent at col. 15, lines 27-32, disclosing the use of a pacemaker or defibrillator & '652 patent at col. 2, lines 55-62, disclosing that electrodes are the source of electrical stimulation). In addition, no prior art reference discloses the patterning of an electrically active material along the natural conductance pathways of the heart or otherwise designing an array of conductive material based on an observed or deduced electrical profile of a subject's heart.

By contrast, the present methods and apparatuses concern implantable scaffolds formed from electrically active material for the conduction or insulation of electrical signals that originate within a subject's own body, i.e., are not artificially generated, for example, by a pacemaker or defibrillator. This feature provides the advantages of reducing the implantation profile and obviating the need for components that are vulnerable to electrical failure. In addition, the inventive scaffolds may be patterned along the physiological conductance pathway of a subject's heart, or may otherwise be designed in response to empirically observed physiological or electronic features of a subject's heart. The design of the presently disclosed arrays may therefore reflect the precise requirements of the heart of a subject in need in order to correct a cardiac conductance disorder and restore the proper cardiac conductance profile of that subject.

A cardiac conductance disorder is any condition in which there is abnormal conductance or an arrhythmogenic region in any part of the specialized conductance system of a subject's heart or abnormal conductance between cardiomyocytes. FIG. 1 depicts a generalized schematic of the specialized conductance system of a human heart, and a cardiac conductance disorder may involve abnormal conductance or an arrhythmogenic region at any one or more locations in a particular subject's cardiac conductance system or abnormal conductance between cardiomyocytes. For example, a cardiac conductance disorder may involve abnormal conductance from the sinoatrial node to the right atrium, or at any location in the right atrium, right to left atrium connections, or left atrium that results in conduction delay of the normal wavefront of depolarization. A cardiac conductance disorder may also involve abnormal conductance through or between the following structures: the atrium, the AV node, HIS bundle, the right and left bundles, the Purkinje network, or the ventricular cardiomyocytes. Abnormal conductance may be continuously (chronically) or intermittently present in the subject's cardiac conductance system. Exemplary cardiac conductance disorders include sino-atrial block, intra-atrial conduction delay, AV node block, right bundle branch block, left bundle branch block, and intra-ventricular conduction delay.

An arrhythmogenic region may be defined as a region of cardiac tissue that participates in initiation or perpetuation of arrhythmias. Initiation of arrhythmias may occur by enhanced automaticity of cardiac cells or afterdepolarizations of cardiac cells in the arrhythmogenic region and serve as a focal source of arrhythmias. Perpetuation of arrhythmias may occur by participation of the arrhythmogenic region in a micro-reentrant or a macro-reentrant circuit. In the case of a micro-reentrant circuit, the cardiac tissue involved with entire circuit would be considered the arrhythmogenic region. A conductance abnormality which results in significant conduction delay is also an arrhythmogenic region which may support perpetuation of a micro-reentrant circuit. An arrhythmogenic region may be identified as a region of cardiac tissue that participates in an arrhythmia based on mapping of an ongoing arrhythmia. An arrhythmogenic region may also be identified in normal rhythm by markers of a conductance abnormality such as complex and fractionated electrograms, reduced electrogram amplitude, and late potentials.

Exemplary cardiac arrhythmias that may occur due to cardiac conduction disorders are atrial fibrillation, atrial flutter, atrial tachycardia, ventricular tachycardia, and ventricular fibrillation. Conduction blocks such as left bundle branch block in the setting of patients with cardiomyopathy results and dyssynchrony and worsening of heart failure. Cardiac conductance disorders may also comprise physical deformities in the subject's heart in at least mesoscopic level that are attributable to abnormal tissue thickness, fibrotic structures, scarring (for example, from previous medical procedures), cardiomegaly such as atrial dilatation or ventricular dilitation, especially left atrial enlargement or left ventricular dilitation. The presently disclosed methods and apparatuses may be used to correct abnormal conductance at any in any part of the conductance system of a subject's heart, and thereby to treat any disorder that arises from one or more conductance abnormalities or arrhythmogenic regions.

Any suitable technique may be used to detect and optionally characterize conductance abnormalities or arrhythmogenic regions in a subject's heart. For example, one may use a conductance map of the subject's heart to identify at least one location of the heart that corresponds to a conductance abnormality. Various systems exist for obtaining conductance maps, for example, in the context of atrial fibrillation ablation. Presently, the most widely used systems include the CARTO system (Biosense Webster, Diamond Bar, Calif.) (see Pappone C, et al., *J Am Coll Cardiol* 2006; 48:2340-2347; Novak P G, et al., *J Cardiovasc Electrophysiol* 2004; 15:967) and the NavX system (Endocardial Solutions, Inc., Minneapolis, Minn.) (see Estner H L, et al., *Electrical isolation of pulmonary veins in patients with atrial fibrillation: reduction of fluoroscopy exposure and procedure duration by the use of a nonfluoroscopic navigation system (NavX). Europace* 2006; 8:583-587). Using known techniques, mapping catheters may be steered to the pulmonary vein in order to obtain a mapping image. Magnetic catheters are presently available on the open market and can provide the requisite accuracy, reachability, and remote navigation characteristics. Such technology may therefore be used to extract impulse propagation characteristics, among other information. Non-invasive mapping of electrical activation may also be performed using an inverse solution from body surface potentials and may be used to identify conductance abnormalities. (C. Ramanathan, R. N. Ghanem, P. Jia, K. Ryu, Y. Rudy, "*Electrocardiographic Imaging (ECGI): A Noninvasive Imaging Modality for Cardiac Electrophysiology and Arrhythmia*" Nature Medicine 2004; 10:422-428)

A conductance map of a subject's heart may be used in the design process of the overall arrangement of the array/apparatus. For example, an array according to the present methods and apparatuses may be arranged so that it at least partially corresponds to a conductance map of a subject's heart. In some embodiments, the conductance map may be used to produce a "generic" array that is then modified according to additional information concerning one or more of the location, size, and type of identified conductance abnormalities. Assessing the type (characterization) of a conductance abnormality is discussed more fully below. Modifications of a generic array may include, at one or more locations of the array, altering the type of material, altering the width, thickness, or another geometric dimension of the material, or altering the correspondence of the array to the conduction map at a particular location in the array.

In addition to identifying at least one location of the subject's heart that corresponds to a conductance abnormality, the present methods may comprise determining one or more characteristics of a conductance abnormality at an identified location of the subject's heart. For example, the magnitude, directionality, conduction velocity, refractory period, peripheral rate and regularity organization (see Krummen D, et al., *Pacing Clin Electrophysiol.* 2009; 32(11):1366-1378, and mass represent parameters of a given conductance abnormality that may be determined in accordance with the present methods, using any suitable sensory device or combination of sensory devices. Devices for characterizing a conductance abnormality include, for example, electrocardiograms and intracardiac electrograms.

Alternatively or in addition to the conductance map of the subject's heart, additional mapping may be performed to identify one or more arrhythmogenic regions of the subject's heart for targeting placement of the conductance modulating material. These arrhythmogentic regions may include, for example, one or more regions identified to contain rotors of continuous electrical activation (for example, a phase singularity); one or more regions with focal sources of rapid electrical activation; one or more regions with continuous electrical activity (for example, complex fractionated atrial electrograms); one or more regions of rapid electrical activation when compared to neighboring regions (for example, dominant frequency); or, one or more regions of atrium with fibrosis as determined by MRI techniques or signal processing intracardiac electrograms.

Alternatively or additionally, one or both of the location and type of conductance abnormalities or an arrhythmogenic region in a subject's heart may be deduced from information that otherwise relates to the cardiac conductance disorder from which the subject is suffering. For example, if a subject is known to be suffering from a cardiac conductance disorder that is known to be characterized by the presence of a particular type of conductance abnormality at a particular location of the heart, the design process for producing the array may include constructing the array so that it includes an appropriate material and structure so that the array that will contact and compensate for the surmised abnormality.

As discussed more fully below, identification of the location, one or more characteristics, or both location and characteristics of a conductance abnormality or an arrhythmogenic region is considered during the design process of the array that comprises a conductance modulating material. In addition, the design process of the array can be influenced by the identification, and if necessary, classification, of the cardiac conductance disorder in the subject. For example, if a subject is known to be suffering from atrial fibrillation, it is possible to classify the atrial fibrillation in accordance with the ACC/AHA/ESC 2006 Guidelines for the Management of Patients with Atrial Fibrillation (see Fuster V, et al., *J Am Coll Cardiol* 2006; 48: e149-246), which specified that atrial fibrillation may be classified as paroxysmal, persistent, or longstanding persistent. In the case of paroxysmal atrial fibrillation, it has been observed that focal sources around the pulmonary vein trigger the fibrillation (see Jais P, et al., *Circulation* 1997; 95:572-576; Haissaguerre M, et al., *N Engl J Med* 1998; 339:659-666). Therefore, the array for a subject experiencing paroxysmal atrial fibrillation would be postulated as comprising of discretely distributed conductivity alternating elements around the pulmonary vein. However, in chronic atrial fibrillation, more complicated fibrillatory patterns have been observed. Most studies have concentrated on spatial and temporal organization during atrial fibrillation, and the multiple wavelet hypothesis for atrial fibrillation has been widely accepted as the dominant atrial fibrillation mechanism, and has been confirmed by experimental work (Moe G K, et al., *Am Heart J* 1964: 200-220; Allessie M A, et al. *Experimental evaluation of moe's multiple wavelet hypothesis of atrial fibrillation.* In: Zipes D P, Jalife J, editors. *Cardiac Electrophysiology and Arrhythmias.* New York: Grune & Stratton, 1985). According to the multiple wavelet hypothesis, atrial fibrillation results from the presence of multiple reentrant wavelets which led to concept of "rotors" occurring simultaneously in the left and right atria. Thus, elimination of those "rotors" requires more sophisticated distribution of portions of a corrective array or multiple corrective arrays throughout the sites of the heart.

The array of the present methods and apparatuses comprises one or more conductance modulating materials. A conductance modulating material is any substance that modulates the conductivity at a location of a subject's heart when placed in physical contact with that location. The conductance modulating material may increase the conductivity at the location, or may decrease the conductivity (increase the electrical resistance) at the location. Such materials are generally said to be "electroactive." Any material may be used that possesses this characteristic and that may be safely delivered to a subject's heart. Thus, the array may include a conductance modulating material that enhances electrical conductivity at a corresponding location of the subject's heart (i.e., at a location of the subject's heart that is in physical contact with that portion of the array when the array is in its fully deployed state and has been moved to a final resting position), may include a conductance modulating material that increases electrical resistance at a corresponding location of the subject's heart, or may include both types of materials. An array according to the present disclosure may therefore comprise at least two materials if the objective is to increase conductivity at one location while increasing resistance at a different location within the subject's heart. Alternatively, the present methods and apparatuses may make use of two or more separate arrays, wherein each of such arrays may comprise one or more conductance modulating materials that respectively increase conductivity or increase resistance.

Exemplary classes of materials include polymers, metals, ceramics, or rubbers. Exemplary polymers are disclosed, for example, in Guimard, et al., *Prog. Polym. Sci.* 32 (2007) 876-921. Electroactive polymers include, for example, any member of the family of ionic polymerimetal composites (IPMC). At least one study has demonstrated the utility of polyaniline (PANI) as an electroactive polymer in the culture of electronically excitable cells for cardiac or neuronal tissue engineering applications (see, e.g., Park H, et al., *Anim.* 2005; 41:188-196, Li M et al., *Biomaterials* 2006; 27:2705-15, Bidez P R et al., *J Biomater Sci Polym Ed* 2006; 17:199-212). Polyaniline is effective for increasing conductance, and a different polymer (or any other suitable material) may be used for inducing resistance at a particular location. Noncrystal or amorphous polymers, particularly such polymers with low dielectric constants, as well as acetylenic polymers, are inactive to electric field such that, when electrically saturated, they are generally electronically inactive. Any electroactive or electronically inactive material may be used, as needed.

Because, as described below, the array may be expandable, the array may comprise a shape-memory material, such as nitinol, or may otherwise comprise a material that is compatible with the expansion of the array. Such materials are commonly used in other implantable devices, including stents, and are well known among those of ordinary skill in the art.

The selection of a conductance modulating material for delivery to an identified location of a subject's heart may be based on at least one determined characteristic of a conductance abnormality or an arrhythmogenic region at the identified location. For example, if the conductance abnormality possesses characteristics that mandate the reduction of conductivity at that location of the subject's heart, then the portion of the array that that corresponds to the location may include a conductance modulating material that increases electrical resistance.

The array is delivered to the subject's heart so that it comes into physical contact with at least one location of the subject's heart that corresponds to a conductance abnormality or an arrhythmogenic region. In an exemplary embodiment, the array is delivered to the subject's heart, for example, through a delivery catheter, while in a collapsed configuration. The delivery catheter may be guided to the subject's heart through the pulmonary vein. When the array exits the delivery catheter, for example, into the left atrium, it assumes an expanded state that represents the implantation configuration. The expansion of the array can cause it to contact at least one portion of the endocardium of the subject's heart. Thus, the array may be arranged in its deployed state to contact at least one location of the subject's heart that corresponds to a conductance abnormality or an arrhythmogenic region. This arrangement is represents a deliberate design characteristic that results from the process of identifying at least one location of the subject's heart that corresponds to a conductance abnormality or an arrhythmogenic region, whether by direct localization of the conductance abnormality or arrhythmogenic region or by deducing the location of the conductance abnormality or arrhythmogenic region, e.g., from the type of cardiac conductance disorder from which the subject as suffering.

In another embodiment, the array may also be delivered to the epicardium of the subject's heart through a surgical or percutaneous approach. Techniques for attaining surgical or percutaneous access to the epicardium are well known among those of ordinary skill in the art. When the array is designed for delivery to the epicardium, it may be deliverable as a single, cohesive structure, or may be deliverable in discrete parts. When the array is deliverable in separate parts, in the implanted state, at least some of the parts that make up the array may be separably or permanently attached to one another. In some embodiments, in the implanted state, at least some of the parts that make up the array may be physically set apart from one another.

Figure 2:
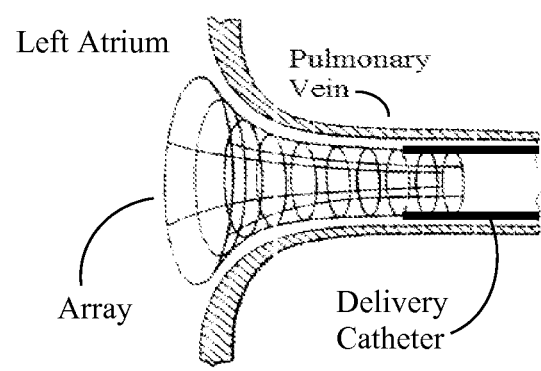
FIG. 2 illustrates one example of how an inventive array can expand upon exiting a delivery catheter in the pulmonary vein.

The array may be delivered to the endocardium of a subject's left atrium. FIG. 2 is a simple depiction of how the array can expand upon exiting the delivery catheter and the pulmonary vein. In the implantation configuration, the array is shaped so that, in its final resting state, it comes into physical contact with at least one location of the subject's heart that corresponds to a conductance abnormality or an arrhythmogenic region. To this end, following initial delivery of the array, it may be necessary to provide positional adjustments so that the array is placed in the proper final resting location. Techniques for positioning and, if necessary, adjusting the position of the array are well known among those skilled in the art, and may be comparable the techniques that are used in connection with other cardiovascular disease therapies, for example, relating to delivering and adjusting the position of a stent or artificial valve.

Following delivery of the array and, as necessary, adjusting the position of the array so that it assumes its correct resting state, the subject's heart may be monitored to assess the effect of the array, i.e., to validate that the array has provided therapeutically beneficial modulation of the one or more identified conductance abnormalities or arrhythmogenic regions in the subject's heart. The array can be said to have provided a therapeutically useful degree of modulation if a statistically significant improvement towards normal conduction is observed at location of the conductance abnormality or arrhythmogenic region, or if a statistically significant improvement in the cardiac conductance disorder is observed. The validation phase may include one, or preferably multiple, measurements of the state of conduction in the subject's heart. The measurements may be performed according to any of the techniques that were suitable for detection and optional characterization of conductance abnormalities or arrhythmogenic regions. For example, just as one may use a conductance map of the subject's heart to identify at least one location of the heart that corresponds to a conductance abnormality or an arrhythmogenic region, one may obtain and assess a further conductance map to validate the efficacy of the array in compensating for one or more of the detected conductance abnormalities or arrhythmogenic regions.

Because certain conductance abnormalities, such as atrial fibrillation, or arrhythmogenic regions are spontaneous and may be complicated by the presence of other diseases, the validation phase should comprise a sufficient period of time for monitoring and evaluation following implantation of the array. For example, it has been observed that although direct current (DC) cardio conversion (a known technique for treating abnormal heartbeats, such as in connection with permanent atrial fibrillation) can appear to restore sinus rhythm in 90% of patients, relapse can occur after an unpredictable period of time that may comprise hours, days or weeks (see Waktare J E P. *Atrial fibrillation. Circulation.* 2002; 106:14-16). Thus, because of the possibility of relapse following a period of time during which the efficacy of the array may otherwise appear to be confirmed, the validation phase should comprise a suitable interval of monitoring and evaluation.

If the results of the validation phase indicate that the array was not sufficient to compensate for one or more of the conductance abnormalities or arrhythmogenic regions, it may first be appropriate to revisit the initial diagnosis of the conductance disorder. A correct diagnosis can contribute significantly to the proper design of a compensating array, at least because the diagnosis provides crucial information, for example, regarding the location and type of conductance abnormalities or arrhythmogenic regions in the subject's heart. If the diagnosis is re-checked and confirmed as correct, then adaptive reprogramming of the array may be required. One approach for adaptive reprogramming is the use of patient based data base of previous electrocardiogram readings to customize the conductivity properties of the compensating network. Once a new array has been designed and produced using data obtained during the validation phase, the existing, implanted array may be collapsed or disassembled and withdrawn from the subject's heart, for example, using the same technique that was used to deliver the array, and the redesigned array may be delivered and implanted in its place. Relative to the original array, a redesigned array may include, at one or more locations of the array, alterations to the type of material, alterations to the width, thickness, or another geometric dimension of the material, or alterations to the correspondence of the array to the conduction map at a particular location in the array. Suitable techniques for collapsing and withdrawing the array will be readily appreciated among those skilled in the art, and may be comparable the techniques that are used in connection with other cardiovascular disease therapies, for example, relating to collapsing and removing a stent or artificial valve, or surgical or percutaneous removal of an implanted material. The present apparatuses and methods therefore take into account the possible need for removing and replacing an array, and are fully compatible with such processes in the event that the validation step or other evaluation of the subject's response to the array reveals that the array was not sufficiently effective.

EXAMPLE 1

Design and Implantation of Array

A subject presenting with cardiac arrhythmia is diagnosed with apparent paroxysmal atrial fibrillation. Using an invasive or non-invasive mapping system such as the CARTO system (Biosense Webster, Diamond Bar, Calif.), a conductance map of the subject's heart is obtained, and the diagnosis is thereby confirmed. Based on the conductance map, an array is constructed from both electronically inactive and electroactive polymer such as found the EPI-FLO device (Electronic Polymers, Inc., Jarrel, Tex.) or others (see, e.g., Rechargeable Lithium Battery Electrodes Using a Multifunctional Polymer Binder, A E Javier, S N Patel, N P Balsara—Meeting Abstracts, 2012). In particular, the array comprises discretely distributed conductivity altering elements that in the implanted state will be positioned at various locations including for example the location of the subject's pulmonary vein. The array is folded and inserted into a delivery catheter, which is delivered with the assistance of a guiding catheter to the subject's pulmonary vein. The distal end of the delivery catheter is advanced to the portion of the pulmonary vein that terminates in the left atrium, and the folded array is advanced to the distal end of the delivery catheter. As the array is advanced beyond the distal end of the delivery catheter and into the left atrium, the array self-expands, and when the array is fully expelled from the delivery catheter it assumes a fully expanded state such that it rests against the endocardium of the left atrium. Using catheter manipulation, the position of the array within the left atrium is assessed and adjusted so that the conductivity altering elements are positioned at the desired location of the subject, e.g., near the pulmonary vein.

After confirmation that the final resting position of the array represents the correct position, the delivery and guiding catheters are removed, and the catheter entry point is closed and sutured. After suitable recovery time, the subject is provided with guidance regarding self-monitoring procedures and regular clinical follow-up, during which time the efficacy of the array is assessed by evaluating whether the subject's heart displays recurrent atrial fibrillation. In the absence of recurrent atrial fibrillation, there are no adjustments of the array.

What is claimed:

1. A method for treating a cardiac conductance disorder in a subject comprising:
   determining a conductance abnormality or an arrhythmogenic region of the subject's heart;
   selecting a conductance modulating material based on an electrical conductance of the conductance modulating material and a determined characteristic of the conductance abnormality at the at least one location of the subject's heart;
   delivering an array comprising the conductance modulating material to the at least one location; and
   modulating conductance to a therapeutically useful degree at the at least one location without chronic artificial electrical stimulation.

2. The method according to claim 1 further comprising using a conductance map of the subject's heart to identify at least one location of the heart that corresponds to a conductance abnormality.

3. The method according to claim 1 further comprising using a map of electrical characteristics of the subject's heart to identify at least one location of the heart that corresponds to an arrhythmogenic region.

4. The method according to claim 1 further comprising determining one or more characteristics of a conductance abnormality at an identified location of the subject's heart.

5. The method according to claim 1 comprising delivering said array to the endocardium of the subject's heart.

6. The method according to claim 5 comprising delivering said array to the subject's heart through a catheter.

7. The method according to claim 4 comprising delivering said array to the endocardium of the subject's left atrium.

8. The method according to claim 1 comprising delivering said array to the epicardium of the subject's heart.

9. The method according to claim 1 wherein the array is expandable.

10. A method for treating a cardiac conductance disorder in a subject comprising:
   determining a conductance abnormality or an arrhythmogenic region in a subject's heart;
   selecting a conductance modulation material to modify electrical conductivity at a corresponding location of said subject's heart based on an electrical conductance of the conductance modulating material and the conductance abnormality or the arrhythmogenic region;
   delivering an array comprising the conductance modulating material to the corresponding location of the subject's heart; and
   modulating conductance to a therapeutically useful degree to said at least one loction without chronic artificial electrical stimulation.

11. A method for treating a cardiac conductance disorder in a subject comprising:
   determining a conductance abnormality or an arrhythmogenic region in a subject's heart;
   selecting a conductance modulating material based on an electrical conductance of the conductance modulating material and an ability of the material to increase electrical resistance at the region;
   delivering an array comprising the conductance modulating material to the region that corresponds to the conductance abnormality or the arrhythmogenic region; and
   modulating conductance to a therapeutically useful degree to said at least one location without chronic artificial electrical stimulation.

12. An apparatus for treating a cardiac conductance disorder in a subject comprising a conductance modulating material that is deployable to at least one location of said subject's heart that corresponds to a conductance abnormality or an arrhythmogenic region, and is arranged in a deployed state to contact said location in order to modulate conductance to a therapeutically useful degree to said at least one location without chronic artificial electrical stimulation, wherein the conductance modulating material is selected based on an electrical conductance of the conductance modulating material and an ability of the material to modify electrical conductivity at a location of said subject's heart that contacts said material.

13. The device according to claim 12 that is self-expanding.

14. An apparatus for treating a cardiac conductance disorder in a subject comprising a conductance modulating material that is deployable to at least one location of said subject's heart that corresponds to a conductance abnormality or an arrhythmogenic region, and is arranged in a deployed state to contact said location in order to modulate conductance to a therapeutically useful degree to said at least one location without chronic artificial electrical stimulation, wherein the conductance modulating material is selected based on an electrical conductance of the conductance modulating material and an ability of the material to increase electrical resistance at a location of said subject's heart that contacts said material.

15. The device according to claim 12 that is arranged to at least partially correspond to a conductance map of said subject's heart.

16. The device according to claim 12 wherein said conductance modulating material comprises an electroactive polymer.

* * * * *